US009962490B2

(12) United States Patent
Karlsson et al.

(10) Patent No.: US 9,962,490 B2
(45) Date of Patent: May 8, 2018

(54) MEDICAMENT DELIVERY DEVICE

(71) Applicant: SHL Group AB, Nacka Strand (SE)

(72) Inventors: Sebastian Karlsson, Sundbyberg (SE); Gunnar Elmén, Huddinge (SE)

(73) Assignee: SHL GROUP AB, Nacka Strand (SE)

( * ) Notice: Subject to any disclaimer, the term of this patent is extended or adjusted under 35 U.S.C. 154(b) by 543 days.

(21) Appl. No.: 14/666,674

(22) Filed: Mar. 24, 2015

(65) Prior Publication Data

US 2015/0196713 A1    Jul. 16, 2015

Related U.S. Application Data

(63) Continuation of application No. 13/577,725, filed on Aug. 14, 2012, now Pat. No. 8,986,245.

(51) Int. Cl.
*A61M 5/20* (2006.01)
*A61M 5/315* (2006.01)
*A61M 5/24* (2006.01)

(52) U.S. Cl.
CPC ........ *A61M 5/2033* (2013.01); *A61M 5/2448* (2013.01); *A61M 5/3157* (2013.01); *A61M 2005/2451* (2013.01); *A61M 2205/581* (2013.01); *A61M 2205/582* (2013.01)

(58) Field of Classification Search
CPC .............. A61M 5/2066; A61M 5/2033; A61M 5/3157; A61M 2005/2073; A61M 2205/581; A61M 2205/582; A61M 5/2448; A61M 2005/2451
See application file for complete search history.

(56) References Cited

U.S. PATENT DOCUMENTS

| 4,755,169 | A | 7/1988 | Sarnoff et al. |
| 6,319,225 | B1 | 11/2001 | Sugita et al. |
| 6,793,646 | B1 | 9/2004 | Giambattista et al. |
| 6,893,420 | B2 | 5/2005 | Arnisolle |
| 8,986,245 | B2 * | 3/2015 | Karlsson ............ A61M 5/2066 604/131 |

(Continued)

FOREIGN PATENT DOCUMENTS

| EP | 1518575 A1 | 3/2005 |
| FR | 2815543 A1 | 4/2002 |

(Continued)

OTHER PUBLICATIONS

Swedish Patent Office, Int'l Search Report in PCT/SE2011/050027, dated May 11, 2011.

(Continued)

*Primary Examiner* — Theodore Stigell
(74) *Attorney, Agent, or Firm* — McDonnell Boehnen Hulbert & Berghoff LLP

(57) ABSTRACT

An injection device with a feedback mechanism includes a housing for a medicament container having a stopper, a plunger rod for acting on the stopper, a button interactively connected to the plunger rod, an activation member having a flexible locking device releasably connected to the plunger rod, a drive force device, a locking member slideably between positions in which the locking member either completely or partially surrounds the flexible locking device, and a guide rod. Audible and tactile information that an injection has started is provided by the plunger rod's hitting the stopper.

5 Claims, 6 Drawing Sheets

(56) References Cited

U.S. PATENT DOCUMENTS

Figure 1:
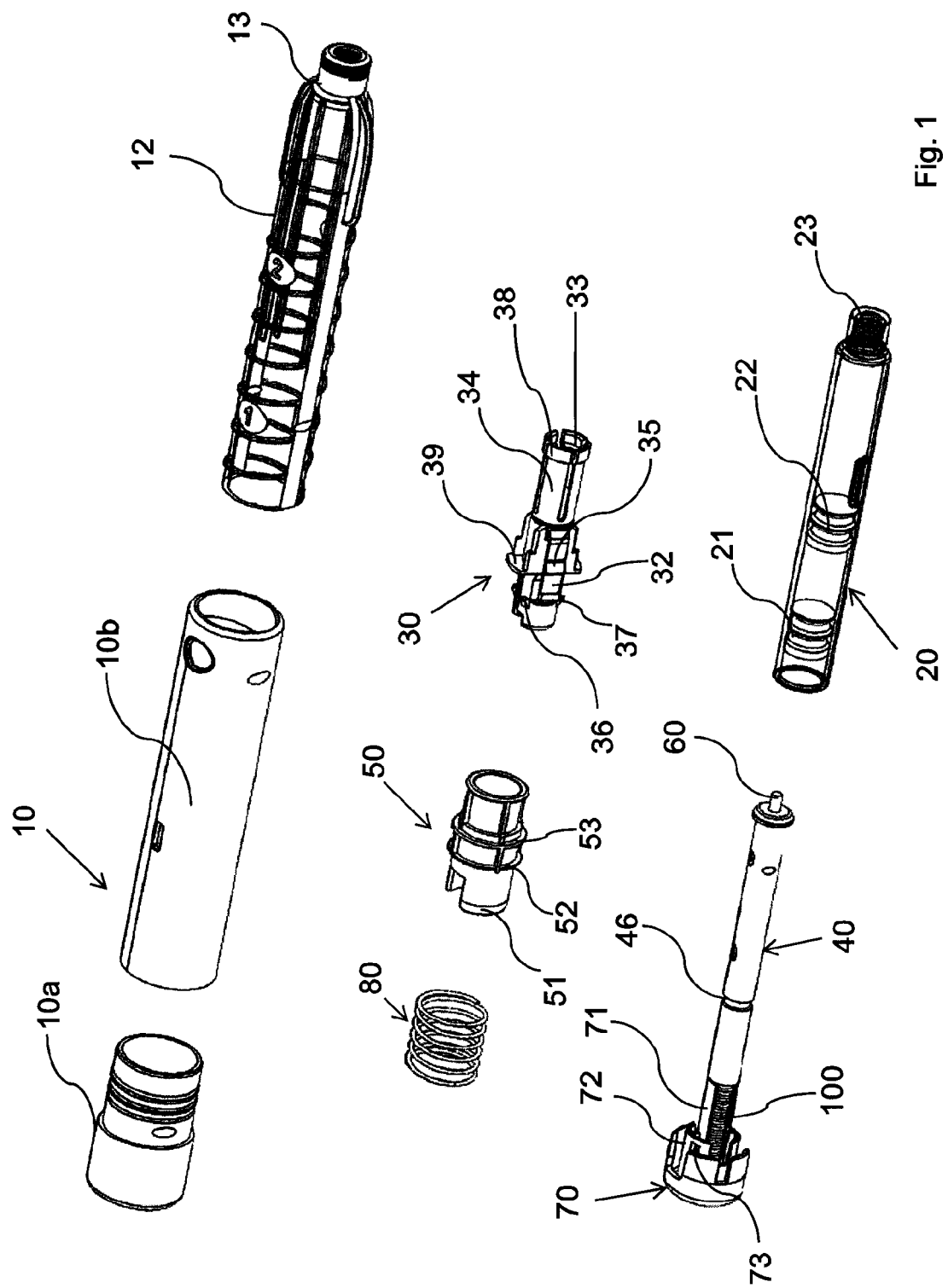

| | | |
|---|---|---|
| 2009/0259181 A1 | 10/2009 | Moser |
| 2012/0184917 A1* | 7/2012 | Bom .................. A61M 5/24 604/187 |
| 2012/0310156 A1 | 12/2012 | Karlsson et al. |

FOREIGN PATENT DOCUMENTS

| | | |
|---|---|---|
| WO | 00/62839 A2 | 10/2000 |
| WO | 2006/080893 A1 | 8/2006 |
| WO | 2009/147026 A1 | 12/2009 |

OTHER PUBLICATIONS

Swedish Patent Office, Written Opinion in PCT/SE2011/050027, dated May 11, 2011.

* cited by examiner

MEDICAMENT DELIVERY DEVICE

The present application is a continuation of U.S. patent application Ser. No. 13/577,725, filed Aug. 14, 2012, now U.S. Pat. No. 8,986,245, which is a U.S. National Phase Application pursuant to 35 U.S.C. § 371 of International Application No. PCT/SE2011/050027 filed Jan. 12, 2011, which claims priority to U.S. Provisional Patent Application No. 61/302,607 filed Feb. 9, 2010 and Swedish Patent Application 1050128-6, filed Feb. 9, 2010. The entire disclosure contents of these applications are herewith incorporated by reference into the present application.

TECHNICAL FIELD

The present invention relates to a medicament delivery device for administering, disposing or delivering medicaments in a safe and reliable way. More particularly, it relates to an injection device for manually penetrating a needle arranged the said device and automatic injecting a drug mixture from a multiple chamber container wherein an audible and a tactile information is provided to the user indicating that the auto-injection has started.

BACKGROUND ART

There are a type of medicaments that can be stored for a long time and that are filed in containers as e.g. cartridges, syringes, ampoules, canisters or the like, containing a ready-to-use medicament in liquid state. However, there are also other types of medicaments that are a mixture of two substances, a medicament agent (e.g. lyophilized, powdered or concentrated liquid) and a diluent (e.g. water, dextrox solution or saline solution), wherein these type of medicaments cannot be pre-mixed and stored for a long time because the medicament agent is unstable and can be degraded and loses its affect quickly. Hence, a user, e.g. a patient himself/herself, a physician, a nurse, hospital personnel or trained persons, has/have to perform the mixing within a limited time period prior to the delivery of a dose of medicament to a patient. Further, some medicament agents are subject to meet significant chemical changes white mixing. Such sensitive medicament agents require a particular treatment so that, when mixing said medicament agents with a diluent, unreasonable mixing force will degrade said medicament agents.

In order to facilitate the mixing, a number of containers for mixing have been developed comprising at least two chambers, known as multi-chamber containers. These multi-chambered containers comprise a first chamber containing the medicament agent and at least a second chamber containing the diluent. These chambers are sealed off with stopper such/so that the medicament agents do not become degraded. When the medicament agent is to be mixed shortly before administering, redirecting passages are opened between the chambers, usually by depressing a distal stopper and in turn a divider stopper of the container somewhat. The passages allow the mixing of the medicament agent and the diluent and the medicament is ready for delivery.

The above mentioned requirements can be achieved by simple medicament delivery devices, such as a common hypodermic syringe, but the procedure is of course rather awkward, in particular for users not used to handle devices. In order to facilitate for the patient themselves to administer the medicament with a predetermined dose in an easy, safe and reliable way and also to facilitate the administration of medicaments for hospital personnel in the same facilitated way, a number of automatic and semi-automatic devices have been developed in combination with these multiple-chamber solutions for obtaining a mixing before delivery.

A self-injection device arranged with a dual-chamber container, wherein both the mixing and the injection are done automatically by mechanical means, as springs and other means, is disclosed in U.S. Pat. No. 4,755,189. A similar solution is disclosed in U.S. Pat. No. 6,793,646 wherein the mixing of a dual-chamber cartridge is done automatically by springs upon activation of the device and the injection is done by manually applying a force to a plunger rod forwardly. A drawback with these devices is that the mixing force, to which medicament agents are subject to, is too high at the beginning due to Hookes law. Hence, the medicament agents can be degraded.

Another solution is disclosed in WO 2004004609, wherein both the mixing and the injection are done automatically by electronics controlled means. A drawback with this device is that the electronics are dependent on batteries and is very sensitive to noise, moisture, water, etc.; which can result in malfunctions. Even more the manufacture of these devices is more expensive than the manufacture of mechanical devices.

In U.S. Pat. No. 6,319,225 the mixing of a dual-chamber ampoule is done manually. The device is set to be vertical on a flat plane and then a downward press on its proximal case causes a relative upward movement of its plunger rod pressing a stopper of the ampoule with eye observation on actions inside the ampoule, such that a mixing is obtained. Though in U.S. Pat. No. 6,319,225 is disclosed that the best suitable process for mixing a medicament agent with a diluent, is by performing manual control of the diluent flow with adequate slowness which will be monitored by eye observation; a drawback with this device is that the mixing force, to which medicament agents are subject to, can be high if the user is stressed and wants to use the device as soon as possible. Hence, the medicament agents can be degraded.

Moreover, the handling and safety aspects of injector devices, having a certain degree of automatic functions, as well as immediate accessibility in emergency situations are issues that attract a lot of attention when developing this type of devices.

One important safety aspect when handling an auto-injector which is used to achieve a manual mixing and an automatic injection, is the locking of the injection means, e.g. a compressed spring actuating on a plunger rod, before the manual mixing have been completed.

One such a device is disclosed in U.S. Pat. No. 6,893,420 wherein a self-injection device is arranged with a dual-chamber body. The mixing is done manually by a screw-tightening operation and the device comprises locking means for locking a latch means that prevent the automatic penetrates and injection means from being released before the mixing has been completely finished. However, this solution is rather bulky and relies also on many components acting in co-operation and in sequence, one triggering another, which may lead to a mal-function, mal-dose accuracy, or that the device becomes complicated, hence not user friendly. This device suffers from the drawback that locking means has to be actively removed from the device after the mixing has been finished. This is a step which is not intuitive for a user, who will try to push the locking means instead of removing them. Another drawback is the dose accuracy, since the penetration starts pushing the stoppers, the medicament will start to be expelled during the whole penetration sequence, leading to so called wet injections and delivering of medicament through the whole penetration tissue instead of injecting the required dose at the intended penetration depth.

Another such a device is disclosed in WO2007/115424A1 which relates to an injection device having a container holder having a multi-chamber container within, which is manually movable relative to the injection device for the purpose of mixing the components within the multi-chamber container. The device further comprises a spring which can bear on a part of the injection device, and a coupling element for coupling the container holder to the spring such that, during the movement of the container holder into the injection device, the spring is tensioned. The device also comprises an activation knob and a push button, wherein the activation knob has to be rotated for forcing the push button to protrude from the housing and thereby setting the device in a ready for injection delivery state. However, this solution suffers from the drawback that the activation knob has to be actively manipulated for releasing the push button after the mixing has been finished. This is a step which is not intuitive for a user, who will try to find where the push button or activation means are located instead of rotating the knob.

Moreover, another device disclosed in WO2009/147026A1, which is an earlier patent application of the present applicant suffer from the problem of indicating the user when the auto-injection has started and also when the auto-injection is finished.

Even though the devices according to U.S. Pat. No. 6,893,420, WO2007/115424A and WO2009/147026A1 have proved to function well and displays a degree of safety, there is always a desire for improvement of such devices, among them being the design of the mechanism in order to simplify the manufacture and assembly in order to reduce costs but at the same time having improved features maintaining or even improving the reliability of the safety and function of the device.

SUMMARY

The various objects and advantages of this invention can be obtained from an injection device having a feedback mechanism, the device being for penetrating a needle arranged to the device into an injection site and automatically injecting a medicament. The device includes:

a housing configured to hold a medicament container having a stopper;

a plunger rod having a proximal end and being configured to act on the stopper;

a button interactively connected to the plunger rod;

an activation member having a tubular flexible locking device releasably connected to the plunger rod;

a drive force device pre-tensionedly arranged between a distal portion of the activation member and the proximal end of the plunger rod;

a locking member coaxially and slideably arranged around the activation member between a first position, in which the locking member completely surrounds the tubular flexible locking device, and a second position, in which the locking member partially surrounds the tubular flexible locking device; and a guide rod coaxially arranged between the distal portion of the activation member and the stopper, the guide rod having a proximal portion that extends beyond the proximal end of the plunger rod. Displacement of the button causes disconnection of the tubular flexible locking device and the plunger rod such that the drive force device causes the proximal end of the plunger rod to hit the stopper, thereby providing audible and tactile information that automatic injection has started.

BRIEF DESCRIPTION OF FIGURES IN THE DRAWINGS

Figure 2:
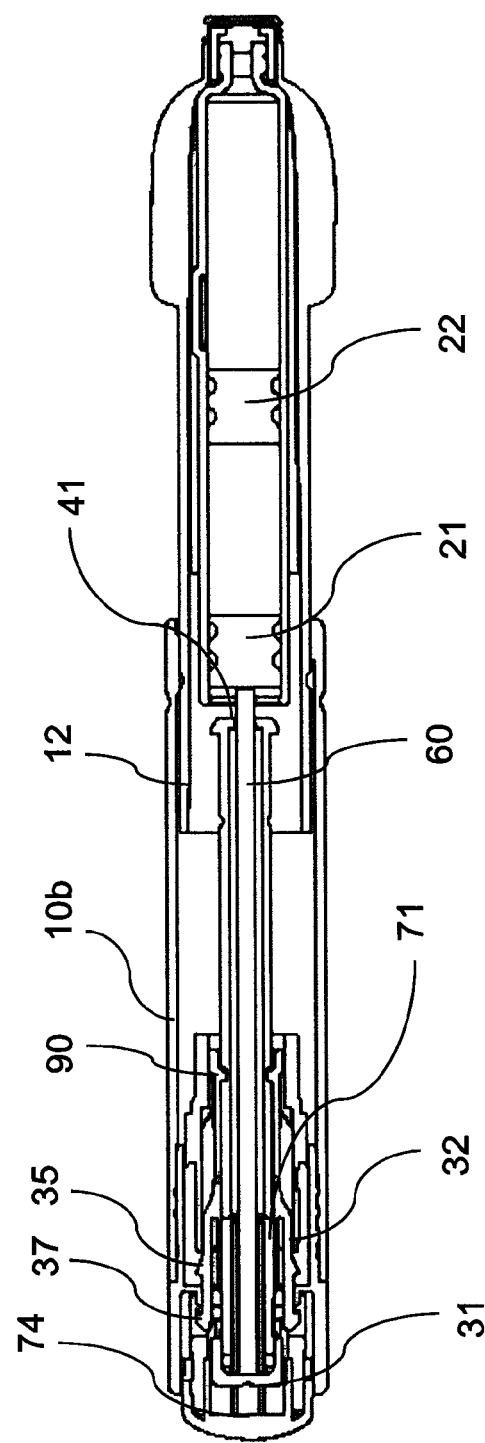
Figure 3:
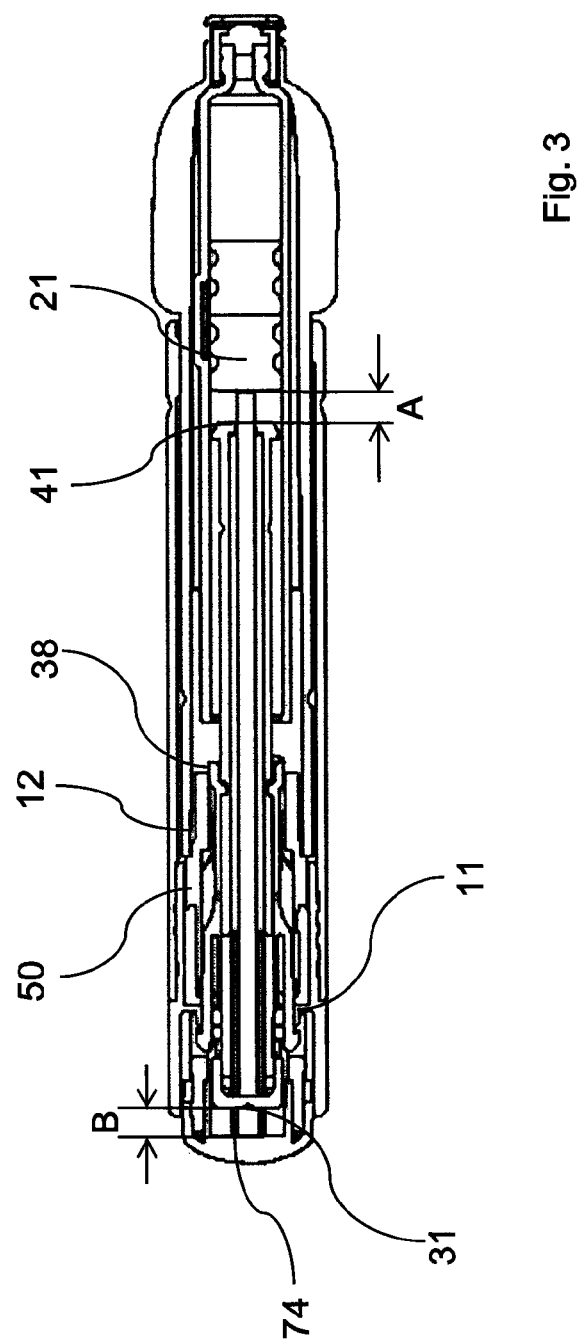
Figure 4:
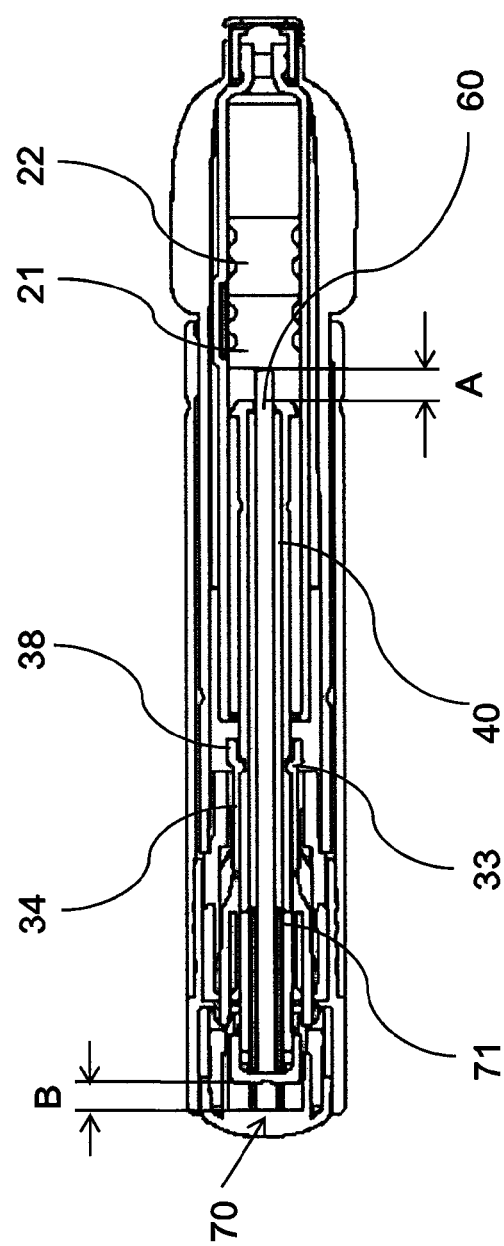
Figure 5:
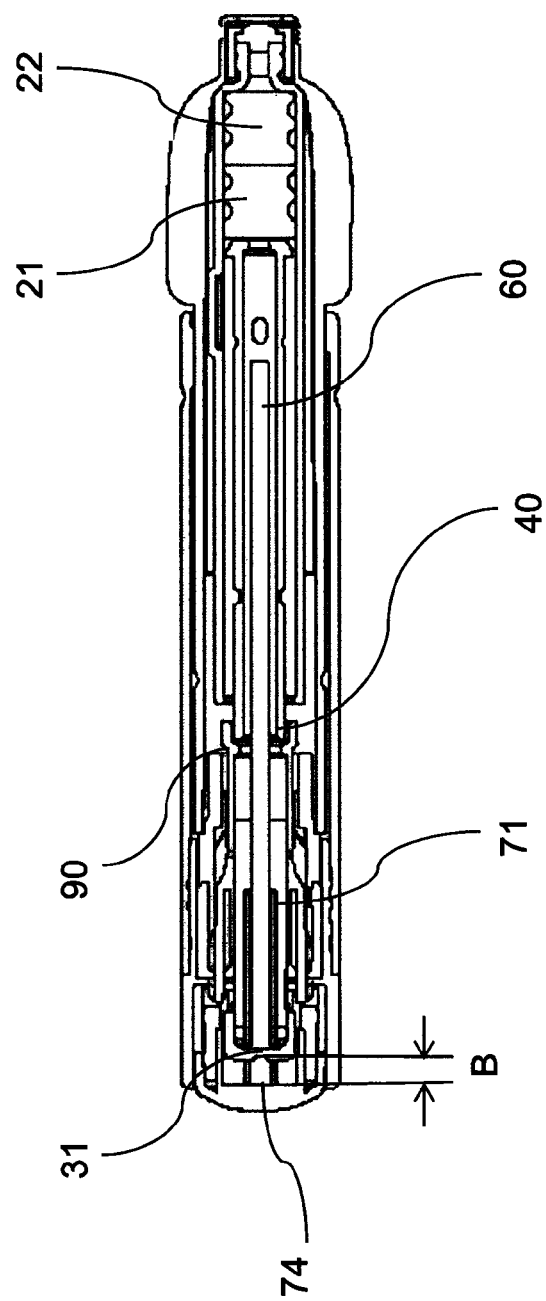
Figure 6:
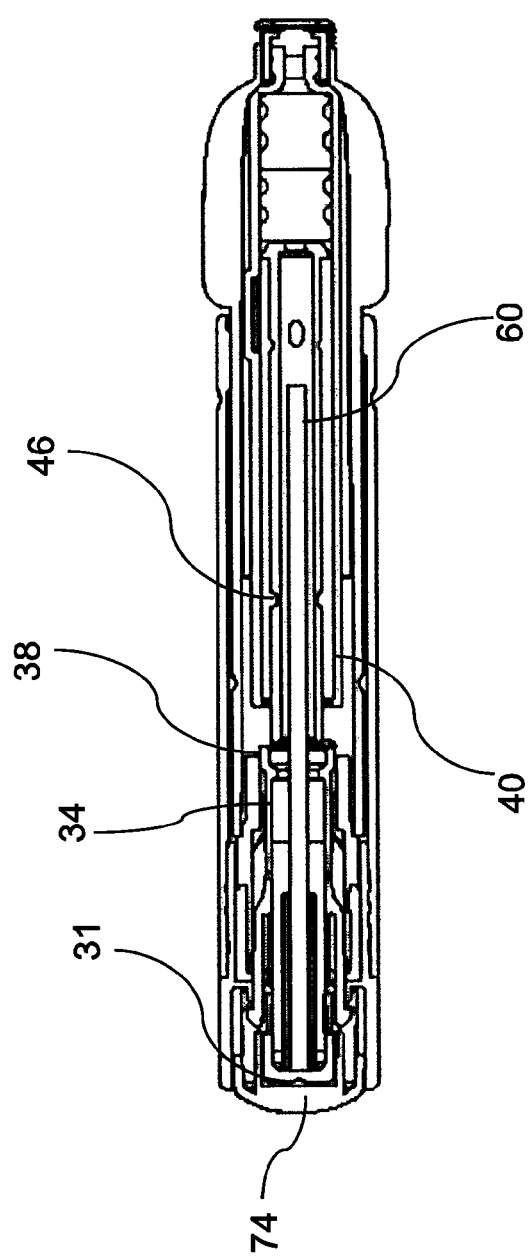

In the following detailed description of the invention, reference will be made to the accompanying drawings, of which FIG. 1 is an exploded view of the auto-injector according to the invention, FIG. 2 is a cross-sectional side view of the auto-injector according to the invention in a pre-mixed position, FIG. 3 is a cross-sectional side view of the auto-injector according to the invention in a medicament mixed position, FIG. 4 is a cross-sectional side view of the auto-injector according to the invention after the push button has been depressed, FIG. 5 is a cross-sectional side view of the auto-injector according to the invention when the auto-injection is almost finished, FIG. 6 is a cross-sectional side view of the auto-injector according to the invention when the auto-injection is finished.

DETAILED DESCRIPTION

In the present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

The present invention relates to an injection delivery device comprising a housing formed by a distal housing part 10 and a proximal housing part 12, and wherein the distal housing part comprises a first distal housing part 10a and a second distal housing part 10b. It is however to be understood that other designs are feasible within the present invention. Further, the outer surface of the proximal housing part is arranged with at least one flexible tongue having an annular protrusion (not shown) which is intended to fit into a corresponding annular recess on the surface of the second distal housing part as will be described below.

The device further comprises a proximal housing part 12 into which a multi-chamber container 20 is arranged and wherein said proximal housing part is arranged to be manually displaced into said distal housing for mixing at least two substances arranged inside said container; a plunger rod 40 arranged to act on a distal stopper 21 which is arranged inside said container; a push button 70 protruding from said distal housing part and being interactively connected to the plunger rod; an activation member 30 comprising tubular flexible locking means 34 releasably connected to said plunger rod; drive force means 100 pre-tensioned arranged between a distal end surface 31 of the activation member and a proximal end wall 41 of the plunger rod; a locking member 50 coaxially arranged around said activation member and being distally slideable in relation to said activation member by said proximal housing between a first position wherein said locking member completely surrounds said tubular flexible locking means holding said plunger rod and thereby said drive force means in a pre-tensioned state and a second position wherein said locking member partially surrounds said flexible locking means; and a guide rod 60 coaxially arranged within the drive force means 100 between the distal end surface 31 of the activation member and the distal stopper 21, and wherein a proximal portion of said guide rod protrudes through the proximal end wall of the plunger rod determining a first predetermined distance "A" between the proximal end wall and the distal stopper, as seen in FIG. 3, such that when said push button is proximally displaced, it forces the plunger rod, the activation member and thereby the guide rod to be proximally displaced, whereby the tubular flexible locking means comes completely out of contact with the locking member and with the plunger rod, primary allowing the plunger rod to be proximally displaced the first predetermined distance by the force of the pre-tensioned drive force means such that the proximal end wall 41 of the plunger rod hits the distal stopper 21 for providing an audible and tactile information that the aromatic injection has started.

The proximal housing part 12 houses the multi-chamber container 20, wherein a proximal neck portion 23 of the multi-chamber container fits into a threaded neck portion 13 of the proximal housing part and wherein said multi-chamber container comprises at least two medicament substances arranged in each chamber, a distal stopper 21, a proximal stopper 22, and redirecting passages between the chambers. Further, the inner surface of the second distal housing part is arranged with threads arranged to interact with corresponding threads arranged on the outer surface of the proximal housing part.

The device further comprises a plunger rod 40 arranged to act on the distal stopper 21 which is arranged inside said container. The plunger rod is formed as a tubular member with an outer diameter somewhat smaller than the inner diameter of the container body to be used.

The push button comprises a distal transversal wall 74 having en inner surface located at a second predetermined distance "B" from the distal end surface 31 of the activation member, as seen in FIG. 3; at least two first proximally extending tongues 71, wherein each tongue has a proximal surface abutting a distal annular surface of the plunger rod; and at least two second proximally extending tongues 72, wherein each tongue comprises at least one longitudinally extending slot 73.

Surrounding the plunger rod is the activation member 30 with a mainly tubular shape. The proximal end of the activation member comprises tubular flexible locking means 34 so as to form flexible tongues. Each tongue has an inclined transition surface 90 which meets with a band-shaped part 38 with enlarged diameter forming the proximal annular surface of the tubular flexible lading means. On the inner surface adjacent the transition surface a generally radial inwards directed ledge 33 is arranged, with a shape as to fit into a groove 46 of the plunger rod. The activation member is further provided with flexible hook means 32 so as to form at least one flexible tongue having a radial outwardly directed hook 37 at its outer end, and having a protrusion 35 with an inclined surface. The flexible hook means 32 are arranged to interact with annular holding means 11 formed as a u-shaped ledge arranged on the inner circumference surface of the first distal housing part. The activation member is also provided with at least one radially outwards directed protrusion 33 interacting with at least one longitudinally extending slot 73 of the push button, such that the activation member is longitudinally movable in relation to said push button. Further, the activation member also comprises at least two oppositely arranged stop ledges 39 directed radially outwards from the outer surface on either side.

The locking member 50 also of a generally tubular form comprises at its distal end at least two oppositely arranged cut-outs of a generally rectangular shape forming at least two distally extending tongues 51, and wherein the widths of said cut-outs correspond to the width of the stop ledges 39 of the activation member. The locking member also comprises a proximal end having a distal annular ledge 52 and a proximal annular ledge 53 on its outer surface.

The device further comprises a compression spring 80 arranged between the at least two oppositely arranged stop ledges 39 of the activation member and the distal annular ledge 52 of the locking member.

The function of the injector according to the invention will now be described in connection with the FIGS. 2-6.

The injector will be delivered to the user as shown in FIG. 2, where the multi-chamber container is placed in the proximal housing part and the distal housing part is attached to the proximal housing part. The tubular flexible locking means 34 are engaged to the plunger rod through the generally radial inwards directed ledges 33 fitting into the groove 46 of the plunger rod. The locking member being coaxially arranged around said activation member in the first position therein said locking member completely surrounds said tubular flexible locking means holding said plunger rod and thereby said drive force means in the pre-tensioned state.

When a mixing is to be performed, the proximal housing part is screwed into the distal housing part until the plunger rod and the guide rods which are static in relation to the proximal housing part, has shifted the distal stopper proximally with respect to the container such that medicament substances inside said multi-chamber container have been completely mixed, see FIG. 3. In this mixed position, the annular protrusion of the at least one flexible tongue on the outer surface of the proximal housing part 12 fits into the corresponding annular recess on the inner surface of the second distal housing part.

At the same time the annular distal end part of the proximal housing part abuts the proximal annular ledge 53 of the locking member and forces said locking member axially towards the distal end of the device against a force of the compression spring. The compression spring is then tensioned. A portion of the band-shaped part 38 is then partially situated outside the proximal annular end of the locking member, as seen in FIG. 4. The at least two distally extending tongues 51 of the activation member will then come in contact with the inclined surface of the protrusion 35 of the hook means 32 on the activation member whereby the hooks 37 are moved radially inwards.

The next step is to connect a needle or a safety pen needle to the proximal end of the proximal housing part, and to achieve a manual penetration of the needle into an injection site as e.g. the tissue of a patient.

When activating the injection device, the user merely depresses the push button, FIG. 4, wherein at the at least two first proximally extending tongues 71 of the push button which are abutting the distal annular surface of the plunger rod, forces the plunger rod to be moved towards the proximal end of the device. Since the plunger rod is connected to the activation member by the generally radial inwards directed ledges 33 fitting into the groove 46 of the plunger rod, the activation member is also forced towards the proximal end of the device, and since the distal end of the guide rod is abutting the distal end surface 31 of the activation member, the guide rod is also force towards the proximal end of the device starting to force the distal stopper 21 towards the proximal end of the device. During the proximal displacement of the activation member, the hooks 37 pass inside the annular holding means 11 which is formed as a u-shaped ledge arranged on the inner circumference surface of the first distal housing part, and the band shaped part 38 comes completely outside the proximal annular end of the locking member. The resilient properties of the tubular flexible locking means 34 of the activation member forces the band shaped part 38 to flex radially outwards causing the ledges 33 to come out of the groove 46 of the plunger rod, which then is free to move due to force of the pre-tensioned drive force means inside the plunger rod. Also when the band shaped part 38 flexes radially outwards, the inclined transition surfaces 90 of the tubular flexible locking means 34 then abut against the proximal annular end of the locking member. The force of the drive force means urges primary the plunger rod to be proximally displaced the first predetermined distance between the proximal end wall of the plunger rod and the distal stopper, such that the proximal end wall of the plunger rod hits the distal stopper producing an audible and tactile indication. The distal stopper forces the proximal stopper proximally and the mixed liquid substance of medicament is injected into the patient tissue until the proximal stopper reaches the inner proximal end of the container, as seen in FIG. 5.

Just before the proximal stopper reaches the inner proximal end of the container, the distal annular surface of the plunger rod passes the proximal annular surface of the tubular flexible locking means 34 coming into the inner circumferential surface of the band shaped part 38 whereby the inclined transition surfaces 90 of the tubular flexible locking means 34 slide over the proximal annular end of the locking member due to a remaining force on the drive force means and the force of the tensioned compression spring 90 forcing the activation member to move distally the second predetermined distance. When the activation member is distally displaced, the at least one radial outwards directed protrusion 36 slides within the at least one longitudinally extending slot 73 of the push button, the stop ledges 39 hits the distal surface of the annular holding means 11 which is formed as a u-shaped ledge arranged on the inner circumference surface of the first distal housing part, and the distal end surface 31 of the activation member hits the inner surface of the transversal wall 74 of the push button producing an audible and tactile indication that the injection is finished.

It is to be understood that the tubular flexible locking means are arranged to be released from said plunger rod only after said locking member is moved from the first position to the second position and said push button is proximally displaced. If the mixing is not completely performed i.e. the proximal housing part has not been completely displaced into the distal housing part such that the annular distal end part of the proximal housing part which abuts on the proximal annular ledge 53 of the locking member has not forced said locking member axially towards the distal end of the device against the force of the compression spring 80 and thereby the flexible hook means 32 has not been flexed radially inwards. Therefore, if the user attempts to depress the push button before the mixing is completely done, the outwardly directed hooks 37 of the flexible hook means 32 will engage the annular holding means 11 which is termed as a u-shaped ledge arranged on the inner circumference surface of the first distal housing part for avoiding premature activation of the device.

It is to be understood that the embodiment described above and shown in the drawings is to be regarded as a non-limiting example of the invention and that it is defined be the patent claims.

What is claimed is:

1. An injection device having a feedback mechanism, the injection device being for penetrating a needle arranged to the device into an injection site and automatically injecting a medicament and comprising:
   a housing configured to hold a medicament container having a stopper;
   a plunger rod having a proximal end and being configured to act on the stopper;
   a button interactively connected to the plunger rod;
   an activation member having a tubular flexible locking device releasably connected to the plunger rod;
   a drive force device pre-tensionedly arranged between a distal portion of the activation member and the proximal end of the plunger rod;
   a locking member coaxially and slidably arranged around the activation member between a first position, in which the locking member completely surrounds the tubular flexible locking device, and a second position, in which the locking member partially surrounds the tubular flexible locking device; and
   a guide rod coaxially arranged between the distal portion of the activation member and the stopper, the guide rod having a proximal portion that extends beyond the proximal end of the plunger rod;
   wherein displacement of the button causes disconnection of the tubular flexible locking device and the plunger rod such that the drive force device causes the proximal end of the plunger rod to hit the stopper, thereby providing audible and tactile information that automatic injection has started.

2. The device of claim 1, wherein the tubular flexible locking device disconnects from the plunger rod only after the locking member moves from the first position to the second position and the button is displaced.

3. The device of claim 1, wherein the plunger rod includes a circumferential groove and the tubular flexible locking device includes tongues having respective inwardly directed ledges configured to fit into the circumferential groove.

4. The device of claim 1, wherein the activation member comprises opposite radially outwardly directed stop ledges, and the locking member comprises distally extending tongues separated by gaps having widths that correspond to widths of the stop ledges.

5. The injection of claim 4, wherein the locking device further comprises an annular ledge, and the injection device further comprises a spring disposed between the stop ledges and the annular ledge.

\* \* \* \* \*